United States Patent
Burk et al.

(10) Patent No.: US 6,486,337 B2
(45) Date of Patent: Nov. 26, 2002

(54) RUTHENIUM-DISPHOSPHINE COMPLEXES AND THEIR USE AS CATALYSTS

(75) Inventors: Mark Joseph Burk, San Diego, CA (US); William Hems, Norwich (GB); Antonio Zanotti-Gerosa, Cambridge (GB)

(73) Assignee: Chirotech Technology Limited, Cambridge (GB)

(*) Notice: Subject to any disclaimer, the term of this patent is extended or adjusted under 35 U.S.C. 154(b) by 58 days.

(21) Appl. No.: 09/821,222

(22) Filed: Mar. 29, 2001

(65) Prior Publication Data

US 2002/0026064 A1 Feb. 28, 2002

(30) Foreign Application Priority Data

Mar. 30, 2000 (GB) .............................. 0007785
Jul. 24, 2000 (GB) .............................. 0018143

(51) Int. Cl.$^7$ .................... C07F 15/00; B01J 31/00; C07C 37/00
(52) U.S. Cl. ..................... 556/22; 556/23; 556/137; 502/155; 568/799
(58) Field of Search ............. 556/22, 23, 137; 568/799; 502/155

(56) References Cited

PUBLICATIONS

Burk et al. (2000), "A Catalyst for Efficient and Highly Enantioselective Hydrogenation of Aromatic, Heteroaromatic, and alpha, beta–Unsaturated Ketones" Organic Letters, vol. 2, No. 26, pp. 4173–4176.*
Ohkuma, T. et al. (1995) "Practical Enantioselective Hydrogenation of Aromatic Ketones" J. Am. Chem. Soc. 117:2675–2676.
Ohkuma, T. et al. (1995) "Preferential Hydrogenation of Aldehydes and Ketones" J. Am. Chem. Soc. 117:10417–10418.
Doucet, H. et al. (1998) "trans–[RuCl$_2$(phosphane)$_2$(1,2–diamine)] and Chiral trans–[RuCl$_2$(diphosphane)(1,2–diamine): Shelf–Stable Precatalysts for the Rapid, Productive, and Stereoselective Hydrogenation of Ketones" Angew. Chem. Int. Ed. 37(12):1703–1707.
Ohkuma, T. et al. (1998) "Asymmetric Hydrogenation of Alkenyl, Cyclopropyl, and Aryl Ketones, RuCl$_2$(xylbinap)(1,2–diamine) as a Precatalyst Exhibiting a Wide Scope" J. Am. Chem. Soc. 120:13529–13530.
Noyori, R. and Ohkuma, T. (2001) "Asymmetric Catalysis by Architectural and Functional Molecular Engineering: Practical Chemo–and Stereoselective Hydrogenation of Ketones" Angew. Chem. Int. Ed. 40:40–73.
Pye, P.J. et al. (1997) "A New Planar Chiral Bisphosphine Ligand for Asymmetric Catalysis: Highly Enantioselective Hydrogenations Under Mild Conditions" J. Am. Chem. Soc. 119:6207–6208.
Pye, P.J. et al. (1998) "[2,2]PHANEPHOS–Ruthenium(II) Complexes: Highly Active Asymmetric Catalysts for the Hydrogenation of β–Ketoesters" Tetrahedron Letters 39:4441–4444.
Ager, D.J. and Laneman, S.A. (1997) "Reductions of 1,3–dicarbonyl Systems with Ruthenium–Biarylbisphopshine Catalysts" Tetrahedron: Asymmetry 8(20):3327–3335.
Rossen, K. et al. (1997) "Kinetic Resolution of rac–4, 12–Dibromo[2.2]paracyclophane in a Palladium [2.2]PHANEPHOS Catalyzed Amination" J. Org. Chem. 62:6262–6263.

* cited by examiner

Primary Examiner—Porfirio Nazario-Gonzalez

(57) ABSTRACT

The present invention concerns novel complexes, suitable in particular for use as catalysts in the asymmetric hydrogenation of ketones, of formula 1

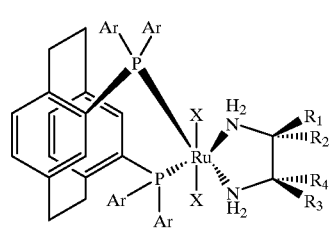

or a diastereoisomer thereof, wherein each Ar is an aromatic or heteroaromatic group of up to 20 atoms;

X is halide or carboxylate; and $R^1$, $R^2$, $R^3$, and $R^4$ are independently hydrogen, aryl or alkyl, optionally linked or part of a ring.

25 Claims, No Drawings

RUTHENIUM-DISPHOSPHINE COMPLEXES AND THEIR USE AS CATALYSTS

FIELD OF THE INVENTION

This invention relates to ruthenium complexes bearing a chiral diphosphine and a chiral diamine and their use as catalysts for asymmetric hydrogenation processes.

BACKGROUND OF THE INVENTION

A large and constantly growing number of catalysts and methodologies are at present available for the homogeneous asymmetric hydrogenation of functionalised ketones. Such ketones bear an auxiliary group that is positioned at the appropriate distance from the carbonyl group and which is capable of binding to the metal of the catalytically active species. This binding arrangement presumably allows chelation of a functionalised ketone to the metal center of the catalyst. The references to these catalysts and methodologies are comprehensively listed by R. Noyori in *Asymmetric Catalysis in Organic Synthesis* (John Wiley & Sons, New York, 1994) and by I. Ojima in *Catalytic Asymmetric Synthesis* (VCH, New York 1994).

Catalytic asymmetric reduction of unfunctionalised ketones presents a greater challenge. Unfunctionalised ketones are those lacking a secondary metal-binding group. EP-A-0718265 describes a method for producing alcohols from carbonyl compounds by hydrogenation in presence of a ruthenium catalyst, a base and a nitrogen-containing additive. When a ruthenium complex bearing a chiral diphosphine was used as catalyst in presence of a chiral diamine and a base, highly productive and enantioselective hydrogenation of aromatic ketones was achieved. Examples of chiral diphosphines examined were BINAP, Tol-BINAP, Xylyl-BINAP, H₈BINAP and CHIRAPHOS Examples of useful chiral diamines were DPEN and DAIPEN. These respective compounds have the formulae

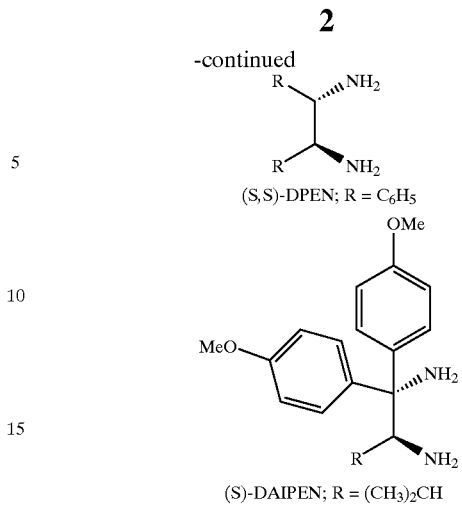

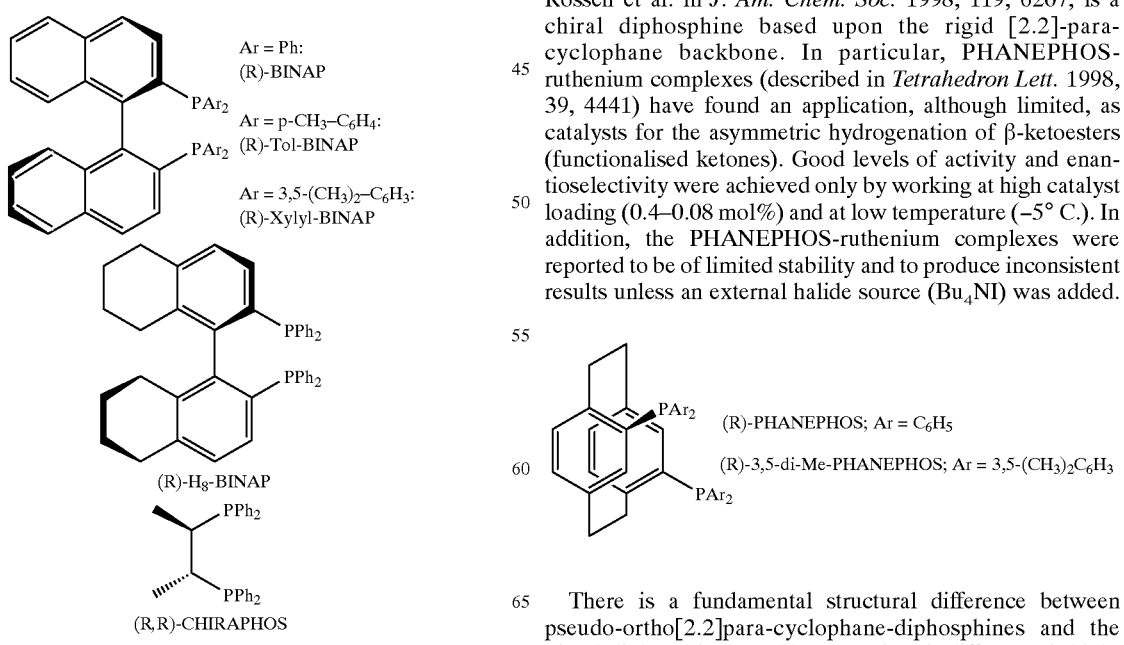

It also has been disclosed by Noyori et al. (*J. Am. Chem. Soc.* 1995, 107, 2675 and 10417) that a diphosphine-ruthenium-diamine complex could be isolated and used as a pre-catalyst for the reduction of aromatic ketones. The use of such a preformed catalyst is advantageous for industrial applications. In particular, high productivity and high enantioselectivity were always associated with the use of the chiral biaryl-phosphines BINAP, Tol-BINAP and Xylyl-BINAP and the chiral diamines DPEN and DAIPEN, Xylyl-BINAP/DAIPEN being the optiumum combination (*Angew. Chem. Int. Ed. Engl.* 1998, 37, 1703 and *J. Am. Chem. Soc.* 1998, 120, 13529). For a review, see also Noyori, *Angew. Chem. Int. Ed.* 2001, 40, 40–73.

A wide array of diphosphines with a chiral backbone different from the biaryl backbone is known (see references listed by Noyori and Ojima in the references mentioned above). So far no chiral diphosphine, other than the BINAP-based ligands indicated above, has been reported to be useful in the efficient and highly enantioselective hydrogenation of unfunctionalised ketones according to the methodology described by Noyori.

PHANEPHOS (structure shown below), first described by Rossen et al. in *J. Am. Chem. Soc.* 1998, 119, 6207, is a chiral diphosphine based upon the rigid [2.2]-para-cyclophane backbone. In particular, PHANEPHOS-ruthenium complexes (described in *Tetrahedron Lett.* 1998, 39, 4441) have found an application, although limited, as catalysts for the asymmetric hydrogenation of β-ketoesters (functionalised ketones). Good levels of activity and enantioselectivity were achieved only by working at high catalyst loading (0.4–0.08 mol%) and at low temperature (−5° C.). In addition, the PHANEPHOS-ruthenium complexes were reported to be of limited stability and to produce inconsistent results unless an external halide source (Bu₄NI) was added.

There is a fundamental structural difference between pseudo-ortho[2.2]para-cyclophane-diphosphines and the biaryl-diphosphines used by Noyori. This difference is highlighted by the contrasting results obtained in the ruthenium-catalysed hydrogenation of β-ketoesters (see data reported in *Tetrahedron Lett.* 1998, 39, 4441 compared with those reported in *Tetrahedron: Asymmetry Report Number* 30, 1997, 20, 3327).

GB-A-2351735 (published Oct. 1, 2001, i.e. after the priority dates claimed herein) discloses the asymmetric hydrogenation of 1-(3,5-bis(trifluoromethyl)phenyl)ethan-1-one, using a ruthenium-phosphine catalyst and a chiral diamine. In the Examples, DIOP is used; in the description, PHANEPHOS is mentioned as one of several possible alternatives. The procedure involves forming the catalyst in situ, the amine being added last.

SUMMARY OF THE INVENTION

This invention is based on the unexpected discovery that the parent ligand PHANEPHOS and its derivatives form stable ligand-ruthenium-diamine complexes of general formula 1

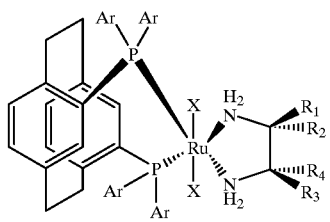

1 wherein each Ar is an aromatic or heteroaromatic group of up to 20 atoms;

X is halide or carboxylate; and $R^1$, $R^2$, $R^3$, $R^4$ are independently hydrogen, aryl or alkyl, optionally linked or part of a ring.

The novel complexes are highly active and enantioselective catalysts for the asymmetric hydrogenation of unfunctionalised ketones, in the present of a catalytic amount of base.

It will be appreciated by those skilled in the art that, rather than use a preformed complex 1, equivalent catalysis may be achieved by forming the catalyst, e.g. the complex 1 or an active species that can be generated therefrom, in situ. This will usually be done by the reaction of the diamine with a ruthenium complex of the ligand in the presence of, or followed by the addition of, the base required for the hydrogenation.

Despite their structural difference, complexes 1 perform as well as, and in several cases better than, the BINAP-Ru complexes described by Noyori as catalysts for the hydrogenation of a wide range of unfunctionalised ketones.

As is evident from the Examples presented below, the PHANEPHOS backbone produces inherently more reactive and selective catalysts then the BINAP backbone. The influence of the Ar substituents on phosphorus is surprisingly less marked and allows for fine-tuning of the catalyst for a particular application Typically, in order to achieve high (>95% ee) enantioselectivity, the choice of BINAP-based catalysts is restricted to those prepared from Xylyl-BINAP and the costly diamine DAIPEN.

In addition, it has been found that the group X does not necessarily have to be a halide, as it transpires from all the examples so far published, but a carboxylate group can be used instead. A compound of general formula 1 where X=$CF_3COO$ has been shown to catalyse the asymmetric hydrogenation of unfunctionalised ketones, giving results comparable to complexes where X=Cl.

DESCRIPTION OF THE INVENTION

The novel ruthenium complex includes a diphosphine moiety that is a (R) or (S)-pseudo-ortho-bisphosphino-[2.2]-para-cyclophane where each phosphorus atom bears two additional aromatic groups. Ar is any aromatic group of up to 10 or 20 carbon atoms and is typically phenyl, optionally bearing one or more substituents. For many applications, the simplest ligand, where Ar=Ph, is applicable. In other applications, it is beneficial to use ligands in which Ar=phenyl substituted with one or more alkyl or alkoxy groups. Particular examples are Ar=3,5-dimethylphenyl, 4-methoxyphenyl and 4-methoxy-3,5-dimethylphenyl. In a preferred embodiment, Ar=3,5-dimethylphenyl (alternatively defined as xylyl) and the phosphine is referred to as 3,5-di-Me-PHANEPHOS.

The chiral diamine is preferably any 1,2-diamine with at least one stereogenic centre and $R^1$, $R^2$, $R^3$, $R^4$ are independently hydrogen or aromatic or alkyl groups, typically of up to 10 or 20 C atoms, optionally linked or part of a ring. Suitable diamines are of formulae 2 to 6

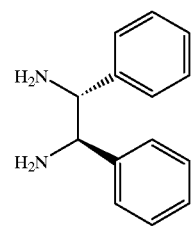

2

(R,R)-DPEN

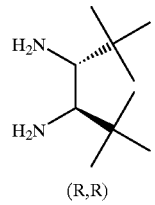

3

(R,R)

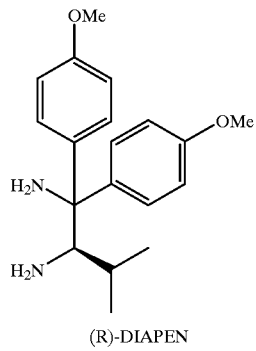

4

(R)-DIAPEN

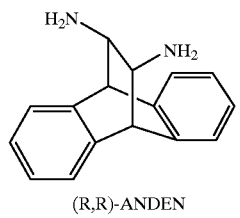

5

(R,R)-ANDEN

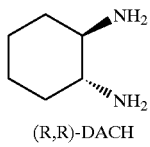

(R,R)-DACH or the opposite enantiomer thereof.

For example, the diamine is DPEN or DACH; both are readily available in either enantiomeric form, and as cheaper than DAIPEN.

X is a halogen atom or carboxylate. Suitable carboxylates are derived from a carboxylic acid of formula $R^5COOH$, wherein $R^5$ is an aromatic or alkyl group of up to 20 atoms, optionally bearing fluorine atoms. For example, X is Cl or $CF_3COO$, and is preferably Cl.

This invention involves the synthesis of ruthenium complexes of general formula 1 and their use as catalysts for asymmetric hydrogenation of ketones in the presence of a base, according to the procedure already described by Noyori (EP-A-0718265; Angew. Chem. Int. Ed. Engl. 1998, 37, 1703; J. Am. Chem. Soc. 1998, 120, 13529). Examples of hydrogenation of acetophenone under different conditions are given below (see Tables 1 and 2). Examples (see Tables 3–5) are also given where a range of differently substituted aromatic ketones and α,β-unsaturated ketones are hydrogenated with high activity (typically, full conversion, 0.0033 mol% catalyst, 0.5–3 hours) and selectivity (typically >97% ee). In such hydrogenations, it is preferred that a particular enantiomer of the disphosphine ligand is matched with the correct enantiomer of the diamine. This is evident from entries 4–7 in Table 2.

Complexes 1 of the present invention are prepared by combining the diphosphine, the diamine and an appropriate ruthenium precursor in a solvent. According to the published literature, diphosphine-ruthenium-diamine complexes 1 may be prepared from [ruthenium-benzene-$Cl_2$]$_2$ in DMP, followed by reaction with the diamine in any suitable solvent, e.g. DMF or dichloromethane. An alternative procedure for the synthesis of complexes of formula 1 (for example where X=Cl) involves initial synthesis of the cationic intermediate [diphosphine-ruthenium-benzene-Cl] Cl which subsequently is reacted with the diamine in DMF (Scheme 1). Such complexes are solids suitable for storage under an inert atmosphere, by that can be handled in air.

Complexes of general formula 1, where X=$CF_3COO$, may be prepared according to a modified procedure, which involves reacting the complex [3,5-di-Me-PHANEPHOS-Ru—(OOCCF$_3$)$_2$]$_2$ (see K. Rossen et al. in *Tetrahedron Lett.* 1998, 39, 4441, for preparation of [PHANEPHOS-Ru—(OOCCF$_3$)$_2$]$_2$) with a diamine in DCM/EtOH (Scheme 2). An example is given where the diamine is DPEN. An example of hydrogenation of acetophenone using this complex is given in Table 2 (final entry).

Scheme 1

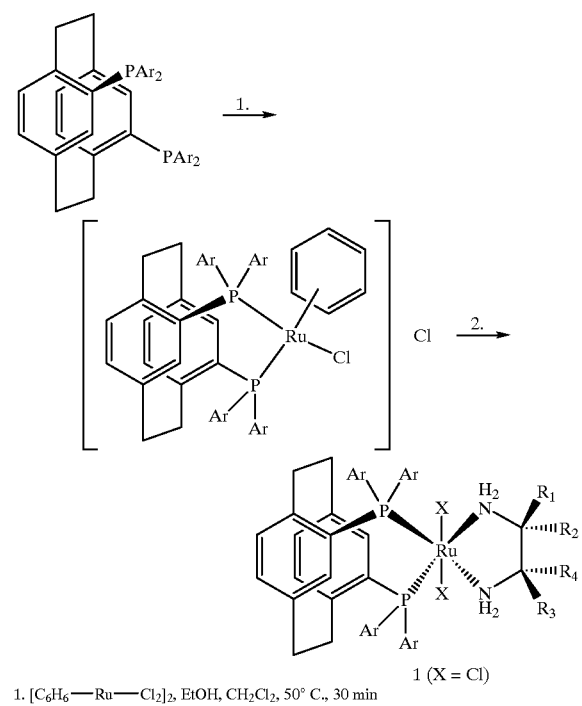

1. [C$_6$H$_6$—Ru—Cl$_2$]$_2$, EtOH, CH$_2$Cl$_2$, 50° C., 30 min
2. Diamine, DMF, 90° C., 20 min Scheme 2

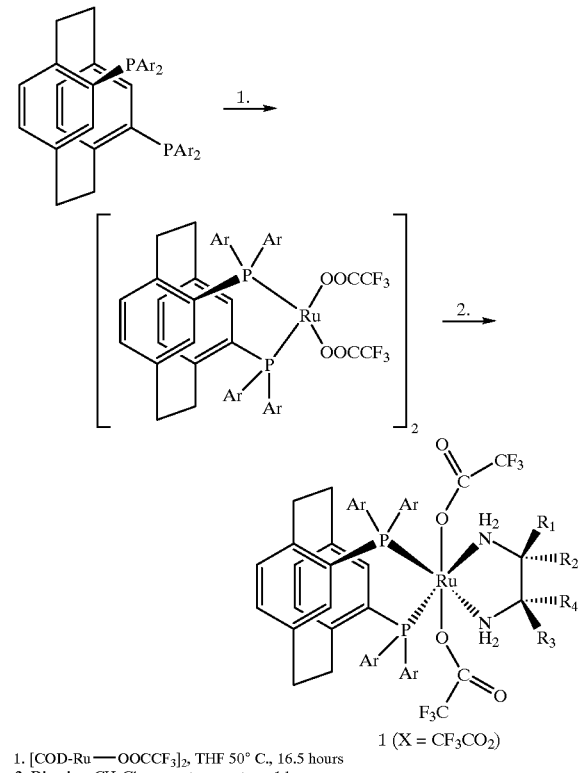

1. [COD-Ru—OOCCF$_3$]$_2$, THF 50° C., 16.5 hours
2. Diamine, CH$_2$Cl$_2$, room temperature, 1 hour A catalyst of the invention is particularly suitable for the stereoselective hydrogenation of a ketone. For example, the ketone has the formula $R^6$—CO—$R^7$, wherein $R^6$ is an aromatic group and $R^7$ is an alkyl group or the formula $R^8$—CO—$R^7$, wherein $R^8$ is alkenyl and $R^7$ is an alkyl group. Such hydrogenation requires a base additive. Typically, the base is an alkali metal alkoxide or hydroxide and is preferably potassium tert-butoxide. At least one molar equivalent of the base relative to the catalyst is used, and typically 10 or 20 to 200 molar equivalents are used. Such hydrogenation reactions may be carried out by procedures that are known to those skilled in the art.

The following Examples illustrate the invention. More specifically:

Examples 1 to 3 illustrate some specific preparations of the ruthenium pre-catalysts derived from 3,5-di-Me-PHANEPHOS.

Examples 4 and 5 illustrate two general procedures for the synthesis of ruthenium pre-catalysts derived from PHANEPHOS and its derivatives. Various procedures are possible, producing equally effective pre-catalysts.

In Example 6 (Table 2), the hydrogenation of acetophenone is used to show that a strong matching/mismatching effect is displayed by a number of different PHANEPHOS derivatives and diamine ligands, the (R)-ligand-(S,S)-diamine diastereoisomer (or the opposite enantiomeric pair) being the most effective combination. In addition, it is apparent that the best results are obtained when the PHANEPHOS derivatives are matched with the diamines DPEN and DACH.

Example 6 (Table 1) compares the results obtained with the catalysts based on the parent ligands PHANEPHOS and BINAP. Rate and selectivity obtainable with the PHANEPHOS catalysts clearly indicate that the effectiveness of the catalyst depends mainly on the structure and chirality of the backbone rather than on the substituents at the phosphorus atom.

Examples 7 to 9 show that the hydrogenation of acetophenone with [3,5-di-Me-PHANEPHOS-Ru—Cl$_2$-DPEN] can be easily and conveniently scaled up, to hydrogenate up to 100 g of substrate at very economical catalyst loadings.

Examples 10 and 11 demonstrate the scope of the hydrogenation catalysed by [3,5-di-Me-PHANEPHOS-Ru—Cl$_2$-DPEN]: a number of aromatic, hetero-aromatic and α,β-unsaturated ketones are smoothly hydrogenated under mild conditions.

Examples 12 and 13 show the advantages obtainable with PHANEPHOS-ruthenium catalysts in the hydrogenation of a specific, sterically hindered substrate, i.e. 2-MeO-acetophenone. Rates, selectivity and catalyst loadings compare very favourably with the results reported in the literature for the best BINAP-ruthenium catalysts.

In Examples 6–13, hydrogenation reactions in which the catalyst contains a (R)-PHANEPHOS ligand give as major product the (R) alcohol. Likewise, the (S) ligand gives primarily the (S) alcohol.

EXAMPLE 1

[(R)-3,5-di-Me-PHANEPHOS-Ru—(OOCCF$_3$)$_2$-(S,S)-DPEN]

[COD-Ru—(OOCCF$_3$)$_2$]$_2$ (26 mg, 0.030 mmol) and (R)-3,5-diMe-PHANEPHOS (41 mg, 0.060 mmol) were placed in a Schlenk tube that was evacuated and filled with nitrogen three times. Anhydrous THF (5 mL) was then added and the resulting yellow solution was heated to 45° C. for 16.5 hours. (S,S)-DPEN (13 mg, 0.06 mmol) was then added and the reaction was stirred at room temperature for 30 minutes. The dark orange solution turned bright yellow. The solvent was removed under vacuum, anhydrous Et$_2$O (5 mL) was added and again removed under vacuum to give a yellow solid residue which was used as hydrogenation catalyst without any further purification. $^{31}$P—NMR (CDCl$_3$, 162 MHz): δ=41 ppm (s).

EXAMPLE 2

[(R)-3,5-diMe-PHANEPHOS-Ru—Cl$_2$-(S,S)-DPEN]

(Procedure A)

[COD-Ru—Cl$_2$]$_2$ (25 mg, 0.05 mmol) and (R)-3,5-di-Me-PHANEPHOS (69 mg, 0.1 mmol) were placed in a Schlenk tube that was evacuated and filled with nitrogen three times. Degassed dichloromethane (4 mL) and EtOH (absolute, 4 mL) were then added and the reaction was heated at 50° C. for 30 minutes to give a deep red/brown solution. The solvent was removed under vacuum, (S,S)-DPEN (21.5 mg, 0.1 mmol) and anhydrous DMF (4 mL) were added. The reaction was heated at 90° C. for 20 minutes. The residue was taken up in Et$_2$O and filtered to remove the insoluble material. The resulting clear yellow solution was concentrated until a yellow solid precipitated. The product was collected by filtration. $^{31}$P NMR (CDCl$_3$, 162 MHz): δ=46 ppm (singlet).

EXAMPLE 3

[(R)-3,5-diMe-PHANEPHOS-Ru—Cl$_2$-(S,S)-DPEN]$_2$ (Procedure B)

[(C$_6$H$_6$)RuCl$_2$]$_2$ (0.436 mmol, 218 mg), (R)-3,5-di-Me-PHANEPHOS (0.871 mmol, 0.60 g), toluene (8 mL) and anhydrous DMF (6 mL) were heated at 100° C. for 4 h To the clear red reaction mixture was added (S,S)-DPEN (0.871 mmol, 185 mg) and the reaction was heated at 100° C. for 1.5 h. The supernatant was separated from the insoluble yellow residue and the solvent was evaporated under reduced pressure. Diethyl ether (10 mL) and methanol (10 mL) were added, a pale yellow precipitate was formed, filtered off and washed with methanol (12 mL). A pale yellow solid was obtained (0.42 g, 45%). $^{31}$P NMR (CDCl$_3$, 162 MHz): d=46 ppm (singlet). The performance in hydrogenation of this isolated precatalyst (B) was indistinguishable from that of the crude precatalyst (A).

EXAMPLE 4

General Synthesis of [PHANEPHOS-Ru—Cl$_2$-Diamine] Complexes (Procedure A)

PHANEPHOS ligand (or derivative) (0.1 mmol) and [(C$_6$H$_6$)RuCl$_2$]$_2$ (0.05 mmol) were dissolved in anhydrous and degassed DMF (2 mL) under nitrogen. The reaction was heated to 100° C. for 3–4 hours, then the diamine (0.105 mmol) was added and the reaction was allowed to reach room temperature while stirring overnight (14–16 hours). The solvent was removed under high vacuum and the crude residue was used for hydrogenations without any further purification.

EXAMPLE 5

General Synthesis of [PHANEPHOS-Ru—Cl$_2$-Diamine] Complexes (Procedure B)

PHANEPHOS ligand (or derivative) (0.1 mmol) and [(C$_6$H$_6$)RuCl$_2$]$_2$ (0.05 mmol) were dissolved in anhydrous toluene (3–5 mL and DMF (0.5–0.8 mL) under nitrogen. The reaction was heated to 100° C. for 3–4 hours and then the diamine (0.105 mmol) was added. The reaction was allowed to reach room temperature while stirring overnight (14–16 hours). The reaction was filtered over Celite to remove turbidity, then the solvent was evaporated under high vacuum and the crude residue was used for hydrogenations without any further purification.

$^{31}$P NMR (162 MHz, CDCl$_3$) of [PHANEPHOS-Ru—Cl$_2$-Diamine] complexes:

[(S)-PHANEPHOS-Ru—Cl$_2$-(S,S)-DPEN]: δ=45.6 ppm (s);
[(S)-PHANEPHOS-Ru—Cl$_2$-(R,R)-DPEN]: δ=45.2 ppm (s);
[(R)-PHANEPHOS-Ru—Cl$_2$-(S,S)-DACH]: δ=45.3 ppm (s);
[(R)-4-MeO-PHANEPHOS-Ru—Cl$_2$-(S,S)-DPEN]: δ=42.8 ppm (s);
[(R)-4-MeO-PHANEPHOS-Ru—Cl$_2$-(S,S)-DACH]: δ=42.8 ppm (s);
[(S)-4-F-PHANEPHOS-Ru—Cl$_2$-(R,R)-DPEN]: δ=44.0 ppm (s);
[(R)-3,5-di-Me-PHANEPHOS-Ru—Cl$_2$-(S,S)-DPEN]: δ=46.1 ppm (s);
[(R)-3,5-di-Me-PHANEPHOS-Ru—Cl$_2$-(S)-DAIPEN]: δ=45.5 ppm (d), 48.9 ppm (d);
[(R)-4-MeO-3,5-di-Me-PHANEPHOS-Ru—Cl$_2$-(S,S)-DPEN]: δ=45.3 ppm (s);

General Procedure for Hydrogenation

All hydrogenations were carried out in a 50 mL Parr hydrogenation vessel equipped with an injection port with a rubber septum for the addition of the solvent using a syringe, a pressure gauge, a tightly fitting removable internal glass liner, a magnetic stirring bar. Commercially available anhydrous i-PrOH was degassed prior to the use by bubbling nitrogen for at least 30 minutes. A commercially available solution of t-BuOK in t-BuOH 1.0 M was used.

EXAMPLE 6

Hydrogenation of Acetophenone at S/C 3000/1

The catalyst (0.002 mmol) was placed in the vessel, which was flushed with nitrogen and then purged at least three times with hydrogen by pressurising to 5.5 bar and releasing the pressure. Then a solution of the substrate (6 mmol, S/C 3000/1) in i-PrOH (3 mL) was added and the reaction was purged again with hydrogen. A solution of t-BuOK in t-BuOH (1.0 M, 0.1 mL) was added, the reaction was purged again, then pressurised to 8 bar of hydrogen and stirred at room temperature until no more hydrogen was consumed. When the pressure was released, a sample of the crude reaction was analysed by chiral GC (DEX-CB column) for conversion and enantiomeric purity. The results are reported in Table 1 (pre-catalysts based on parent PHANEPHOS and bis-aryl phosphines) and in Table 2 (pre-catalysts based on PHANEPHOS derivatives).

TABLE 1 acetophenone → 1-phenylethanol
catalyst, s/c 3000/1, i-PrOH, t-BuOK, b/c 50/1, RT, 120 psi H$_2$

| Catalyst | Time | Conv (%) | Ee (%) |
|---|---|---|---|
| (S)-PHANEPHOS-Ru-Cl$_2$-(S, S)-DPEN | 75 min | 100 | 43 |
| (R)-PHANEPHOS-Ru-Cl$_2$-(S, S)-DPEN | 15 min | 100 | 98 |
| (R)-PHANEPHOS-Ru-Cl$_2$-(S, S)-DACH | 30 min | 100 | 97.5 |
| (R)-BINAP-Ru-Cl$_2$-(R, R)-DPEN | 9 hours | 100 | 84 |
| (S)-BINAP-Ru-Cl$_2$-(S, S)-DACH | 3 hours | 85 | 82 |
| (R)-BINAP-Ru-Cl$_2$-(R)-DAIPEN | 60 min | 100 | 86 |
| (S)-Tol-BINAP-Ru-Cl$_2$-(S, S)-DPEN | 3 hours | 86 | 82 |
| (R)-MeO-BIPHEP-Ru-Cl$_2$-(R, R)-DPEN | 12 hours | 100 | 84 |

TABLE 2 acetophenone → 1-phenylethanol
catalyst, s/c 3000/1, i-PrOH, t-BuOK, b/c 50/1, RT, 120 psi H$_2$

| Catalyst | Time | Conv (%) | Ee (%) |
|---|---|---|---|
| (S)-4-MeO-PHANEPHOS-Ru-Cl$_2$-(R, R)-DPEN | 10 min | 100 | 97 |
| (S)-4-MeO-PHANEPHOS-Ru-Cl$_2$-(R, R)-DACH | 10 min | 100 | 96 |
| (S)-4-F-PHANEPHOS-Ru-Cl$_2$-(R, R)-DPEN | 60 min | 100 | 96 |
| (S)-3,5-di-Me-PHANEPHOS-Ru-Cl$_2$-(S, S)-DPEN | 60 min | 100 | 41 |
| (R)-3,5-di-Me-PHANEPHOS-Ru-Cl$_2$-(S, S)-DPEN | 30 min | 100 | 99 |
| (S)-3,5-di-Me-PHANEPHOS-Ru-Cl$_2$-(S, S)-DACH | 2 hours | 100 | 8 |
| (S)-3,5-di-Me-PHANEPHOS-Ru-Cl$_2$-(R, R)-DACH | 30 min | 100 | 98 |
| (R)-3,5-di-Me-PHANEPHOS-Ru-Cl$_2$-(S)-DAIPEN | 2 hours | 100 | 80 |
| (R)-4-MeO-3,5-di-Me-PHANEPHOS-Ru-Cl$_2$-(S, S)-DPEN | 2 hours | 100 | 99 |
| (R)-3,5-di-Me-PHANEPHOS-Ru-(CF$_3$COO)$_2$-(S, S)-DPEN | 60 min | 100 | 96.5 |

EXAMPLE 7

Hydrogenation of Acetophenone at S/C 10000/1

The same procedure as in Example 6 was used Reactants etc: [(R)-3,5-di-Me-PHANEPHOS-Ru—$Cl_2$-(S,S)-DPEN] (2.1 mg, 0.002 mmol), acetophenone (2.40 g, 20 mmol), i-PrOH (10 mL), t-BuOK in i-PrOH (1 M, 0.5 mL, 0.5 mmol), room temperature, 1 hour, 5.5 bar initial hydrogen pressure, the reaction was periodically recharged with hydrogen to maintain the pressure between 3.5 and 5 5 bar. (R)-1-phenylethanol: >99% conversion, 99% ee.

EXAMPLE 8

Hydrogenation of Acetophenone at S/C 20000/1

The same procedure as in Example 6 was used. Reactants etc: [(R)-3,5-di-Me-PHANEPHOS-Ru—$Cl_2$-(S,S)-DPEN] (2.1 mg, 0.002 mmol), acetophenone (4.80 g, 40 mmol), i-PrOH (8 mL), t-BuOK in i-PrOH (1 M, 1 mL, 1 mmol), room temperature, 1.5 hours, 5.5 bar initial hydrogen pressure, the reaction was periodically recharged with hydrogen to maintain the pressure between 3.5 and 5.5 bar. (R)-1-phenylethanol: >99% conversion, 99% ee.

EXAMPLE 9

Hydrogenation of Acetophenone at S/C 40000/1

A solution of acetophenone (96.1 g, 0.8 mol, stirred over $K_2CO_3$, filtered and freshly distilled) in anhydrous i-PrOH (150 mL) was charged into a 600 mL hydrogenation vessel equipped with mechanical stirrer. The vessel was evacuated and refilled with nitrogen three times, then purged with hydrogen by pressurising to 8 bar (under stirring) and releasing the pressure. The procedure was repeated five times. The vessel was thermostated at 25° C. [(R)-3,5-di-Me-PHANEPHOS-Ru—$Cl_2$-(S,S)-DPEN] (21 mg, 0.02 mmol) was placed in a 50 mL Schlenk flask under nitrogen and a solution of t-BuOK in i-PrOH (1 M, 20 mL, 20 mmol) was added. The reaction was stirred to allow complete dissolution of the solid and the resulting clear yellow solution was transferred into the hydrogenation vessel with a syringe through the injection port. The vessel was purged three times with hydrogen and pressurised to 8 bar. The reaction was stirred at 25° C. and periodically recharged with hydrogen in order to maintain the pressure between 7 and 8 bar. After 4 hours the pressure was released and analysis of the crude by chiral GC indicated that (R)-1-phenylethanol was formed with >99% conversion and 98.5% ee. The solvent was evaporated and the product was obtained as a colourless oil by short path distillation (93.6 g, yield 97%, 98.5% ee, $[a]_D^{20}$=43.36° (neat)).

EXAMPLE 10

Hydrogenation of Other (Hetero)Aromatic Ketones

Reactions were performed according to the same procedure as in Example 6, with 1.0–2.0 M solutions of ketone in i-PrOH with added t-BuOK (base/Ru=50/1) at 18–25° C. and 5.5–8 bar intial hydrogen pressure. All reactions were performed with pre-catalysts [(R)-3,5-di-Me-PHANEPHOS-Ru—$Cl_2$-(S,S)-DPEN] at S/C=3000/1, unless otherwise noted. Reactions were allowed to proceed to completion over 0.5–2.5 hours unless otherwise noted. Enantiomeric excess was determined by chiral GC or chiral HPLC. Results are shown in Table 3. In all cases, the (S) enantiomer is the major product. The substrates are as follows:

TABLE 3

| Catalyst | Ketone | S/C | Time | Ee (%) |
|---|---|---|---|---|
| (S)-3,5-di-Me-PHANEPHOS-Ru-$Cl_2$-(R, R)-DPEN | 0.292 | 3000/1 | <2.5 h | 97 |
| (S)-3,5-di-Me-PHANEPHOS-Ru-$Cl_2$-(R, R)-DPEN | 7b | 3000/1 | <2.5 h | 99 |
| (S)-3,5-di-Me-PHANEPHOS-Ru-$Cl_2$-(R, R)-DPEN | 7c | 3000/1 | <2.5 h | 97 |
| (S)-3,5-di-Me-PHANEPHOS-Ru-$Cl_2$-(R, R)-DPEN | 7d | 3000/1 | <2.5 h | 99 |
| (S)-3,5-di-Me-PHANEPHOS-Ru-$Cl_2$-(R, R)-DPEN | 7 | 3000/1 | <2.5 h | 98 |
| (S)-3,5-di-Me-PHANEPHOS-Ru-$Cl_2$-(R, R)-DPEN | 7f | 3000/1 | <2.5 h | 97 |
| (S)-3,5-di-Me-PHANEPHOS-Ru-$Cl_2$-(R, R)-DPEN | 7g | 3000/1 | <2.5 h | 99 |
| (S)-3,5-di-Me-PHANEPHOS-Ru-$Cl_2$-(R, R)-DPEN | 7h | 500/1 | 2.5 h | 94 |
| (S)-3,5-di-Me-PHANEPHOS-Ru-$Cl_2$-(R, R)-DPEN | 0.333 | 3000/1 | <2.5 h | 98 |
| (S)-3,5-di-Me-PHANEPHOS-Ru-$Cl_2$-(R, R)-DPEN | 8b | 3000/1 | <2.5 h | 96 |
| (S)-3,5-di-Me-PHANEPHOS-Ru-$Cl_2$-(R, R)-DPEN | 8c | 3000/1 | <2.5 h | 98 |
| (S)-PHANEPHOS-Ru-$Cl_2$-(R, R)-DPEN | 8d | 3000/1 | <2.5 h | 71 |
| (S)-3,5-di-Me-PHANEPHOS-Ru-$Cl_2$-(R, R)-DPEN | 0.375 | 3000/1 | <2.5 h | 98 |
| (S)-3,5-di-Me-PHANEPHOS-Ru-$Cl_2$-(R, R)-DPEN | 9b | 3000/1 | <2.5 h | 99 |
| (S)-3,5-di-Me-PHANEPHOS-Ru-$Cl_2$-(R, R)-DPEN | 9c | 3000/1 | <2.5 h | 92 |
| (S)-3,5-di-Me-PHANEPHOS-Ru-$Cl_2$-(R, R)-DPEN | 9d | 3000/1 | <2.5 h | 96 |
| (S)-3,5-di-Me-PHANEPHOS-Ru-$Cl_2$-(R, R)-DPEN | 9 | 3000/1 | <2.5 h | 96 |
| (S)-3,5-di-Me-PHANEPHOS-Ru-$Cl_2$-(R, R)-DPEN | 9f | 3000/1 | <2.5 h | 98 |
| (S)-3,5-di-Me-PHANEPHOS-Ru-$Cl_2$-(R, R)-DPEN | 9g | 1500/1 | 18 h | 78 |
| (S)-3,5-di-Me-PHANEPHOS-Ru-$Cl_2$-(R, R)-DPEN | 9h | 1500/1 | 18 h | 99 |
| (S)-3,5-di-Me-PHANEPHOS-Ru-$Cl_2$-(R, R)-DPEN | 9i | 1000/1 | 16 h | 96 |
| (S)-3,5-di-Me-PHANEPHOS-Ru-$Cl_2$-(R, R)-DPEN | 9j | 3000/1 | <2.5 h | 97 |

TABLE 3-continued

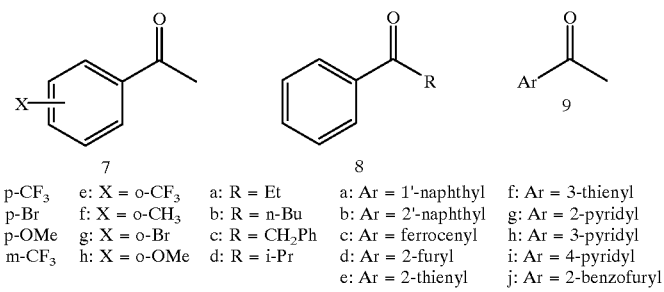

| 7 | | 8 | | 9 | |
|---|---|---|---|---|---|
| a: X = p-CF$_3$ | e: X = o-CF$_3$ | a: R = Et | a: Ar = 1'-naphthyl | f: Ar = 3-thienyl |
| b: X = p-Br | f: X = o-CH$_3$ | b: R = n-Bu | b: Ar = 2'-naphthyl | g: Ar = 2-pyridyl |
| c: X = p-OMe | g: X = o-Br | c: R = CH$_2$Ph | c: Ar = ferrocenyl | h: Ar = 3-pyridyl |
| d: X = m-CF$_3$ | h: X = o-OMe | d: R = i-Pr | d: Ar = 2-furyl | i: Ar = 4-pyridyl |
| | | | e: Ar = 2-thienyl | j: Ar = 2-benzofuryl |

EXAMPLE 11

Hydrogenation of α,β-Unsaturated Ketones

Following the general procedure of Example 6 the reactions were conducted with 1.0 M solutions of ketone in i-PrOH with added t-BuOK (base/Ru=50/1) at 18–25° C. and 5.5 bar intial hydrogen pressure. Substrates 10–11 were reduced with full conversion to the corresponding allylic alcohols. No over-reduction of the alkene functionality was observed. Results are reported in Table 4.

TABLE 4

| Catalyst | Ketone | S/C | Time | Ee (%) |
|---|---|---|---|---|
| (R)-PHANEPHOS-Ru-Cl$_2$-(S, S)-DACH | 10 | 3000/1 | 2 h | 96 |
| (S)-3,5-di-Me-PHANEPHOS-Ru-Cl$_2$-(R, R)-DPEN | 10 | 3000/1 | 1 h | 97 |
| (S)-3,5-di-Me-PHANEPHOS-Ru-Cl$_2$-(R, R)-DACH | 10 | 3000/1 | 18 h | 85 |
| (S)-3,5-di-Me-PHANEPHOS-Ru-Cl$_2$-(R, R)-DPEN | 11 | 1000/1 | 2 h | 94 |

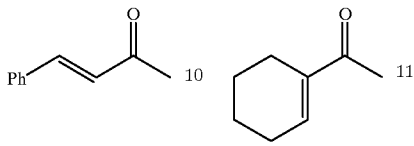

EXAMPLE 12

Hydrogenation of 2-MeO-acetophenone at S/C 2000/1

The catalyst (0.002 mmol) was placed in the vessel, which was flushed with nitrogen and then purged at least three times with hydrogen by pressurising to 5.5 bar and releasing the pressure. Then a solution of the substrate (4 mmol, S/C 2000/1) in i-PrOH (3 mL) was added and the reaction was purged again with hydrogen. A solution of t-BuOK in t-BuOH (1.0 M, 0.1 mL) was added, the reaction was purged again, then pressurised to 4 bar of hydrogen and stirred at room temperature until no more hydrogen was consumed. When the pressure was released, a sample of the crude reaction was analysed by chiral GC (DEX-CB column) for conversion and enantiomeric purity. The results are reported in Table 5 (the results for Xyl-BINAP are obtained from the literature).

TABLE 5

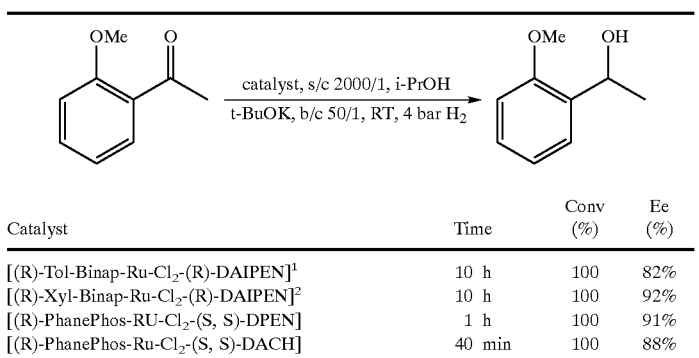

| Catalyst | Time | Conv (%) | Ee (%) |
|---|---|---|---|
| [(R)-Tol-Binap-Ru-Cl$_2$-(R)-DAIPEN][1] | 10 h | 100 | 82% |
| [(R)-Xyl-Binap-Ru-Cl$_2$-(R)-DAIPEN][2] | 10 h | 100 | 92% |
| [(R)-PhanePhos-RU-Cl$_2$-(S, S)-DPEN] | 1 h | 100 | 91% |
| [(R)-PhanePhos-Ru-Cl$_2$-(S, S)-DACH] | 40 min | 100 | 88% |

TABLE 5-continued

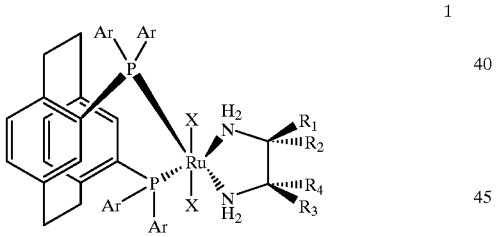

| Catalyst | Time | Conv (%) | Ee (%) |
|---|---|---|---|
| [(S)-MeO-Ph-PhanePhos-Ru-Cl$_2$-(R, R)-DPEN] | 40 min | 100 | 89% |
| [(R)-Xyl-PhanePhos-Ru-Cl$_2$-(S, S)-DPEN] | 2.5 h | 72 | 94% |
| [(S)-MeO-Xyl-PhanePhos-Ru-Cl$_2$-(R, R)-DPEN] | 3 h | 91 | 96% |

[1] Noyori, *Angew. Chemie Ed. Int.* 1998, 1703.
[2] Noyori, *JACS* 1998, 13529, supplementary material

[1] Noyori, *Angew. Chemie Ed. Int* 1998, 1703. [2] Noyori, *JACS* 1998, 13529, supplementary material

EXAMPLE 13

Hydrogenation of 2-MeO-acetophenone at S/C 5000/1

The same procedure as in Example 6 was used. Reactants etc: [(R)-3,5-di-Me-PHANEPHOS-Ru—Cl$_2$-(S,S)-DPEN] (5.4 mg, 0.005 mmol), 2-MeO-acetophenone (3.75 g, 25 mmol), i-PrOH (5 mL), t-BuOK in i-PrOH (1 M, 0.5 mL, 0.5 mmol), room temperature, 8 hours, 8 bar initial hydrogen pressure; the reaction was periodically recharged with hydrogen to maintain the pressure between 3 and 4 bar. (R)-2'-MeO-1-phenylethanol: >99% conversion, 96% ee.

What is claimed is:

1. An enantiomerically enriched ligand-RuX$_2$-diamine complex of formula 1

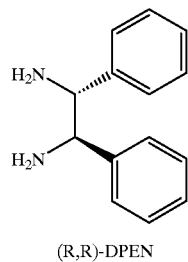

or a diastereoisomer thereof, wherein
   each Ar is an aromatic or heteroaromatic group of up to 20 atoms;
   X is halide or carboxylate; and
   $R^1$, $R^2$, $R^3$, and $R^4$ are independently hydrogen, aryl or alkyl, optionally linked or part of a ring.

2. The complex according to claim 1, wherein Ar is phenyl optionally bearing one or more substituents.

3. The complex according to claim 2, wherein Ar is phenyl bearing one or more electron-rich substituents.

4. The complex according to claim 3, wherein the electron-rich substituents are selected from the group consisting of alkyl and alkoxy.

5. The complex according to claim 2, wherein Ar is phenyl, 4-methoxyphenyl, 4-methoxy-3,5-dimethylphenyl or 3,5-dimethylphenyl.

6. The complex according to claim 1, wherein the diamine component is chiral, and at least one of the amine-bearing centers is stereogenic.

7. The complex according to claim 6, wherein the diamine is a compound of any of formulae 2, 3, 4, 5, or 6

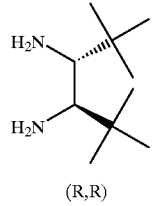

(R,R)-DPEN

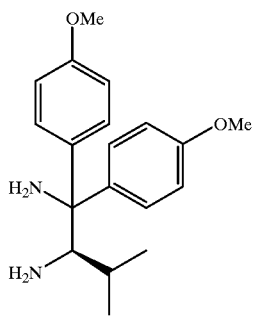

(R)-DIAPEN

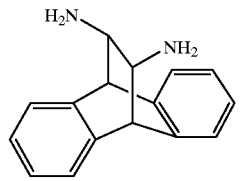

(R,R)-ANDEN

-continued

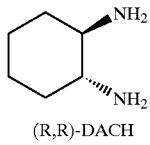

(R,R)-DACH or the opposite enantiomer thereof.

8. The complex according to claim 7, wherein the diamine is the diamine of formula 2 or its opposite enantiomer.

9. The complex according to claim 7, wherein the diamine is the diamine of formula 6 or its opposite enantiomer.

10. The complex according to claim 8, wherein the absolute configuration of the ligand is (R) and the absolute configuration of the diamine is (S,S), or the opposite enantiomeric pair.

11. The complex according to claim 9, wherein the absolute configuration of the ligand is (R) and the absolute configuration of the diamine is (S,S), or the opposite enantiomeric pair.

12. The complex according to claim 1, wherein X is a halogen atom.

13. The complex according to claim 12, wherein X is Cl.

14. The complex according to claim 1, wherein X is the carboxylate anion of a carboxylic acid of formula $R^5COOH$, wherein $R^5$ is an aromatic or alkyl group of up to 20 atoms, optionally bearing fluorine atoms.

15. The complex according to claim 14, wherein X is $CF_3COO$.

16. A method for the stereoselective hydrogenation of a ketone, which is conducted in the presence of base and, as catalyst, a complex according to claim 1.

17. A method for the stereoselective hydrogenation of a ketone, which is conducted in the presence of a base and, as a catalyst, a complex formed in situ from a diamine and a ruthenium complex of a ligand, the ligand and the diamine being as defined in claim 1.

18. The method according to claim 16, wherein the ketone has the formula $R^6$—CO—$R^7$, wherein $R^6$ is an aromatic group and $R^7$ is an alkyl group.

19. The method according to claim 17, wherein the ketone has the formula $R^6$—CO—$R^7$, wherein $R^6$ is an aromatic group and $R^7$ is an alkyl group.

20. The method according to claim 16, wherein the ketone has the formula $R^8$—CO—$R^7$ wherein $R^8$ is alkenyl and $R^7$ is an alkyl group.

21. The method according to claim 17, wherein the ketone has the formula $R^8$—CO—$R^7$ wherein $R^8$ is alkenyl and $R^7$ is an alkyl group.

22. The method according to claim 16, wherein the base is an alkali metal alkoxide or hydroxide.

23. The method according to claim 22, wherein the base is potassium tert-butoxide.

24. The method according to claim 16, wherein the amount of base is 1 to 200 molar equivalents relative to catalyst.

25. The method according to claim 16, wherein the amount of base is 20 to 200 molar equivalents relative to catalyst.

* * * * *